United States Patent [19]

O'Sullivan et al.

[11] 4,243,578

[45] Jan. 6, 1981

[54] DENTAL FILLING COMPOSITION

[75] Inventors: Denis J. O'Sullivan; Bernard J. Bolger; T. Eisirt Casey, all of Dublin, Ireland

[73] Assignee: Loctite Corporation, Newington, Conn.

[21] Appl. No.: 112,878

[22] Filed: Jan. 17, 1980

Related U.S. Application Data

[63] Continuation of Ser. No. 800,599, May 25, 1977, abandoned, which is a continuation of Ser. No. 415,454, Nov. 16, 1972, abandoned.

[30] Foreign Application Priority Data

Nov. 16, 1972 [IE] Ireland ............................... 1580/72

[51] Int. Cl.³ ............................................... C08K 3/40
[52] U.S. Cl. ............................ 260/42.52; 260/998.11; 433/228; 525/455; 525/920; 528/75
[58] Field of Search ....................... 260/42.52, 998.11; 525/455, 920; 528/75

[56] References Cited

U.S. PATENT DOCUMENTS

| | | | |
|---|---|---|---|
| 3,297,745 | 1/1967 | Fekete et al. | 260/471 |
| 3,425,988 | 2/1969 | Gorman | 260/31.2 N |
| 3,629,187 | 12/1971 | Waller | 260/998.11 |
| 3,825,518 | 7/1974 | Foster et al. | 260/998.11 |

*Primary Examiner*—James H. Derrington
*Attorney, Agent, or Firm*—Jean B. Mauro; J. Rodney Reck

[57] ABSTRACT

An improved dental filling material is prepared from polymerizable urethane-acrylate resins which cure by a free-radical mechanism to form hard and durable filling compositions which bond strongly and adhesively to tooth enamel, to dentin, to dental prostheses and to preexisting dental filling materials.

1 Claim, No Drawings

DENTAL FILLING COMPOSITION

This is a continuation, of application Ser. No. 800,599 filed May 25, 1977 now abandoned, which is a continuation of application Ser. No. 415,454, filed Nov. 16, 1972, now abandoned.

BACKGROUND OF THE INVENTION

This invention relates to a novel dental filling composition. In particular, it relates to a dental filling composition which bonds strongly and adhesively to tooth enamel, to dentin, to dental prostheses and to preexisting dental fillings both conventional and of the present invention, in addition to forming a hard mass for space filling in dental cavities and the like.

Most conventional dental restorative filling materials have the serious disadvantage that they do not form strong or durable adhesive bonds to the natural tooth materials to which they are commonly applied, namely tooth enamel and dentin. For this reason it is standard practice to undercut cavities and boreholes before filling them, and thus to lock the moulded and set filling material mechanically in place. While undercutting inherently involves the removal of healthy tooth structure, such procedure has been necessary since fillings in non-undercut cavities would be subject to almost immediate failure.

The older types of dental filling materials, consisting of mercury amalgams, have a tendency to corrode at the interface with a tooth, and the corrosion products formed a seal preventing the ingress of saliva and decay-causing bacteria. However, the mercury and many of its corrosion products are themselves toxic and were also capable of having a deleterious effect on natural tooth material, so that this method of "sealing" the gap between filling and tooth was less than satisfactory. Amalgam fillings also suffered from excessive visibility and never matched the tooth color or surface texture.

Dental inorganic sealant and filling compositions, and the newer and more popular organic polymer filling materials, do not corrode and do not form strong and durable bonds to tooth structure. Therefore, indigenous oral and food-borne bacteria, together with saliva and the products of salivary digestion, easily invade the gap between these inorganic or polymeric sealant or filling compositions and the tooth material beneath it, leading in time to well-known secondary cariogenic processes with consequent eventual enlargement of the tooth cavity and the necessity to replace the filling or remove the tooth. Frequently inorganic filling materials utilize acidic curing agents, which produce trauma in the tooth structure and, hence, are undesirable from this point of view.

A recently introduced dental adhesive called polycarboxylate cement (aqueous polyacrylic acid and zinc oxide) has been shown to adhere efficiently to tooth enamel, but not to dentin. Reports of materials claimed to be capable of bonding adhesively or chemically to dentin are few, and include the following:

(1) Buonocoro, M., Wiloman, W., and Brudevold, F. A., Report on a Resin Composition Capable of Bonding to Human Dentin Surfaces, J. Dent. Res. 35:846-851, 1956.

(2) Galligan, J. D., Schwarts, A. M. and Minor, F. W., Adhesive Polyurethane Liners for Anterior Restorations. J. Dent. Res. 47:629-632, 1968.

(3) Buonocoro, M. G., Bonding to Hard Dental Tissues in 'Adhesion in Biological Systems.' Rd. R. S. Manly, Academic Press, 1970, p. 225-254.

(4) Khowassah, M. A., and Shippy, R. L., In Vitro Investigation of the Adhesive Strength of Cyanoacrylate Bonds to Human Hard Tooth Structures. J. Biomed. Mat. Res. 5 (1971) 159-168.

THE INVENTION

This invention deals with a novel sealing or filling composition for dental applications which utilizes a polymerizable urethane-acrylate monomer of the type described herein, said monomer containing at least two reactive acrylic functional groups and at least two urethane linkages per molecule. It has been found that a monomer of this type, when polymerized in situ in a dental application of the type described herein through its acrylic functional groups will produce a polymer which strongly and adhesively bonds to tooth enamel and dentin, as well as to essentially all dental prostheses and preexisting dental fillings. Polymerization is induced by a free-radical method, involving either the use of an ultra-violet (hereafter "uv") activated free-radical generator, or a peroxy compound in combination with a known activator for said peroxy compound.

This invention also involves a dental filling composite which utilizes the above-described urethane acrylate monomer and curing agents, in combination with an inorganic filling material.

This invention also involves a process for filling apertures or cavities in tooth surfaces which involves filling said aperture or cavity with the above-described composition, and curing said composition in situ.

DISCUSSION OF THE INVENTION AND ITS PREFERRED EMBODIMENTS

Every embodiment of the invention disclosed herein contains a polymerizable urethane-acrylate monomer as described herein. It is understood that certain of these monomers may, in fact, be oligomers or other low polymers of the urethane-acrylate monomer which contain at least two acrylic functional groups, and all such materials are considered to meet the definition of urethane-acrylate monomer as discussed and used herein.

The urethane-acrylate monomers most commonly used in the compositions and process of this invention are substances having structures which allow them to be regarded as the reaction product of an organic polyisocyanate with a polymerizable acrylate ester having a hydroxy or a primary or secondary amino group in the alcoholic moiety thereof. The active hydrogen atom in the alcoholic portion of the ester reacts with the isocyanate group, producing the polymerizable urethane-acrylate monomer used herein.

The acrylates which may be used in making the urethane-acrylate monomer are substances of the general formula $$CH_2=CR^2.COOR^3 \qquad (I)$$

in which $R^2$ is H, $CH_3$, $C_2H_5$ or Cl and $R^3$ is one of the following: (a) a $C_{1-8}$ hydroxyalkyl or aminoalkyl group, (b) a $C_{1-6}$ alkylamino-$C_{1-8}$ alkyl group; or (c) a hydroxyphenyl, an aminophenyl, a hydroxynaphthyl or an aminonaphthyl group which may be further substituted by an alkyl, alkylamino or dialkylamino group, each alkyl group in this sub-part (c) containing up to about 3 carbon atoms.

These acrylates are exemplified by, but not limited to, 2-hydroxyethyl acrylate, 2-hydroxyethyl methacrylate, 2-aminopropyl methacrylate, hydroxyhexyl acrylate, 2-tert-butylaminoethyl methacrylate and hydroxyoctyl methacrylate.

In a convenient and known process for making the polymerizable monomer used in the polymerizable composition according to this invention, an acrylate of general formula I is reacted with a di- or other polyisocyanate, preferably in the presence of a solvent, at a temperature in the range of 0°-200° C. as will be described in more detail later, chosen to suit the specific reactants involved.

The polyisocyanates which may be used in making the polymerizable monomer may be generally represented by the formula $(O=C=N)_n Q$, in which n is an integer from 2 to about 20, preferably 2 to about 5, and Q is an organic radical having a molecular weight up to about 5000 and a bonding capacity equal to n. A preferred class of isocyanates are those of the formula:

$$(O=C=N)_n R^4 \qquad (II)$$

wherein n is 2 and $R^4$ is a $C_{2-20}$ alkylene, alkenylene or cycloalkylene radical or a $C_{6-40}$ arylene, alkarylene, aralkarylene, alkyloxyalkylene or aryloxyarylene radical which may be substituted by 1-4 chlorine atoms or by 1-3 amino or mono- or di-$C_{1-3}$-alkylamino or $C_{1-3}$ alkoxy groups.

Typical examples of such isocyanates are toluene diisocyanates, 4,4'-diphenyl diisocyanate, 4,4'-diphenyl methane diisocyanate, dianisidine diisocyanates, 1,5-naphthalene diisocyanate, 4,4'-diphenyl ether diisocyanate, p-phenylene diisocyanate, trimethylene diisocyanate, tetramethylene diisocyanate, hexamethylene diisocyanate, ethylene diisocyanate, cyclohexylene diisocyanates, nonamethylene diisocyanate, octadecamethylene diisocyanate, 2-chloropropane diisocyanate, 2,2'-diethyl-ether diisocyanate, 2-(dimethylamino) pentane diisocyanate, tetrachlorophenylene-1,4-diisocyanate, 3-heptene diisocyanate and transvinylene diisocyanate.

Other polyisocyanates which may be used are the higher molecular weight polyisocyanates obtained by reacting polyamines containing terminal primary or secondary amine groups, or polyhydric alcohols, for example, the alkane and alkene polyols such as glycerol, 1,2,6-hexanetriol, 1,5-pentenediol, ethylene glycol, polyethylene glycol, "bisphenol-A" and substituted "bisphenol-A" with an excess of any of the above-named diisocyanates. These higher molecular weight urethane or ureide polyisocyanates may be represented by the formula:

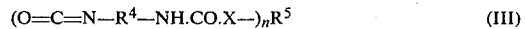

$$(O=C=N-R^4-NH.CO.X-)_n R^5 \qquad (III)$$

in which $R^4$ has the meaning given above; X represents O or $NR^6$ where $R^6$ is H or a $C_{1-7}$ alkyl group; and $R^5$ is the non-functional residue of a polyamine or a polyhydric alcohol having at least n primary or secondary amino or hydroxyl groups respectively; and n is an integer from 2 to 20.

Accordingly, when the monomer is derived from one of the simple diisocyanates defined above, it has the general formula:

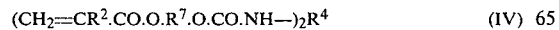

$$(CH_2=CR^2.CO.O.R^7.O.CO.NH-)_2 R^4 \qquad (IV)$$

in which $R^2$ and $R^4$ have the meanings given above and $R^7$ represents $R^3$ less one hydrogen atom. Preferred monomers conforming to this definition include derivatives of higher alkylene diisocyanates such as octamethylene diisocyanate, and the aromatic diisocyanates containing more than 8 non-isocyanate-group carbon atoms, such as durene diisocyanate, i.e., tetramethylphenyl-1,4 diisocyanate, and 4,4'-diphenyl diisocyanate. When, on the other hand, the monomer is derived from one of the higher molecular weight urethane or ureide polyisocyanates aforesaid, it has the general formula:

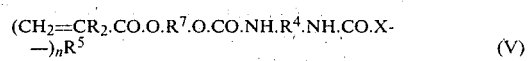

$$(CH_2=CR^2.CO.O.R^7.O.CO.NH.R^4.NH.CO.X--)_n R^5 \qquad (V)$$

in which $R^2$, $R^4$, $R^5$, $R^7$, X and n have the meanings given above.

As used herein, the term urethane denotes a compound having in the molecule the characteristic group —O—CO—NH— and the term ureide denotes a compound having in the molecule the characteristic group —NH—CO—NH—.

A typical and preferred monomer useful in the polymerizable composition of this invention is the monomer of formula IV in which $R^2$ is $CH_3$, $R^7$ is n—$C_3H_6$ and $R^4$ is

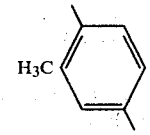

An acrylate is, as stated above, reacted with a polyisocyanate to form a monomer for use in the polymerizable composition of the invention. While the proportions of the reactants used are not critical, it is generally preferred to use about a 0.1 equivalent excess of acrylate ester above the amount needed to react substantially all of the isocyanate groups with a hydroxyl or amino group of the acrylate ester.

The reaction may be carried out in the presence or absence of a solvent. Preferably solvents selected from the aliphatic, cycloaliphatic and aromatic hydrocarbons, for example, benzene, toluene, cyclohexane, hexane and heptane, are employed, but other solvents such as methyl isobutyl ketone, diamyl ketone, isobutyl methacrylate, and cyclohexyl methacrylate can also be utilized if desired, especially where complete compatibility with the dental adhesive is desired. The chief reason for using a solvent is to prevent the reaction mixture from becoming too viscous.

The temperature employed in the reaction may vary over a wide range. Where the reactants are present in approximate chemically equivalent amounts or with slight excess of the acrylate reactant, useful temperatures lie in a range extending from about 10° to 175° C.

When the simpler isocyanates are used the reactants are preferably at or near room temperature, e.g., from 20° C. to 30° C. In the preparation of the high molecular weight monomers using an excess of the acrylate, the reactants may be combined at room temperature but it is preferable to allow them to react at a temperature in the range 40° to 150° C., a specially preferred range having been found to extend from 90° to 120° C. Further detail may be found in U.S. Pat. No. 3,425,988.

Reaction proceeds with a slight elevation of the temperature and is complete when heat ceases to be evolved. The reaction mixture is then cooled at room temperature; if the solvent used is suitable for incorporation in the polymerizable composition according to this invention, the reaction product will need no extraction or purification and is ready for use.

To provide the necessary curing ability to the above-described urethane-acrylate monomer, a suitable initiator system is used in conjunction therewith. If the monomer is to be cured by a uv activation mechanism, a uv activated free-radical generator is selected, and generally may be incorporated directly into the urethane-acrylate monomer. For example, it is possible to use a metal carbonyl of the formula $M_x(CO)_y$, wherein M is a metal atom, preferably Cr, Mn, Fe, Co, Ni, or Mo, x is 1 or 2, and y is an integer determined by the total valence of the metal atoms, generally from 4 to 10. The preferred uv activated free-radical generators are selected from: (a) $C_{1-16}$ straight or branched chain alkyl diones; and (b) carbonyl compounds of the general formula:

$$R(CO)R^1$$

in which R is a $C_{1-10}$ alkyl, aryl, aralkyl or alkaryl radical, and $R^1$ is R or H. R or $R^1$ can contain any substituents which do not adversely affect the compound in serving its intended function. For example, R or $R^1$ can be alpha-substituted with an alkyl, aryl, alkaryl alkoxy or aryloxy radical, or with an amino or a mono- or dialkylamino derivative thereof, each of the above substituents containing up to about six carbon atoms. In addition, R and $R_1$, taken together with the carbonyl group to which they are attached, may represent an aromatic or heterocyclic ketone containing up to about sixteen (16) carbon atoms.

Preferred polymerization initiators are acetophenone, benzophenone and 1- and 2- acetonaphtone. Others are 2,3-butadione, 2,4-dimethyl-3-pentanone, 1- and 2-naphthaldehyde, p-phenylacetophenone, n-proprionophenone, fluoren-9-one, xanthen-9-one and 4,4'-bis-dimethylaminobenzophenone. Uv initiators generally are used at a level between about 0.1% and 7% by weight of the urethane-acrylate monomer, and preferably between about 0.2% and 4.0% by weight.

When cure is to be initiated by free-radical mechanism which is not uv dependent, the urethane-acrylate monomer is used is combination with a peroxy compound and an activator for said peroxy compound. The specific peroxy compound and activator therefor are determined by the speed of cure desired in the final dental sealing or filling composition. This speed of cure also can be varied by the appropriate balancing of concentrations of monomer, peroxy compound and activator therefor. Organic hydroperoxides and organic peresters can be used in the compositions and processes of this invention, particularly those having a molecular weight between about 90 and about 800, preferably between 90 and 400. Typical examples are t-butylperbenzoate, cumene hydroperoxide and t-butylhydroperoxide. These initiators generally are used at a level between about 0.5 and 10% by weight of the urethane-acrylate monomer, preferably 1% to 5% by weight.

The peroxy compounds of the preceding paragraph frequently can be activated by the use of organic sulfimides (such as benzoic sulfimide) and/or primary, secondary or tertiary amines (preferably those to be described hereafter). Typically, these activators are used at a level between about 0.1 and about 7% by weight of the urethane-acrylate monomer, preferably 0.2% to 4% by weight. Alternatively, low levels of transition metal compounds frequently can be used, commonly at a level between about 1 and 1000 parts per million by weight of the urethane-acrylate monomer. Most typically the transition metal is selected from the class consisting of copper, iron, manganese and cobalt.

The most highly preferred peroxy initiator system is obtained by the use of a peroxy initiator selected from the class consisting of acyl peroxides and silyl peroxides. The acyl peroxides have the general formula:

$$Ar.CO.O_2.CO.Ar$$

where each Ar is an aryl radical containing up to about 10 carbon atoms and preferably is $C_6H_5$, $ClC_6H_4$, $NO_2C_6H_4$, or $Cl_2C_6H_3$. The silyl peroxides have the general formula:

$$CH_2\!=\!CH\!-\!Si(OOR^8)_3$$

in which $R^8$ is a $C_{1-6}$ straight or branched chain alkyl radical. The preferred compounds from each group are benzoyl peroxide and vinyl tris(tert-butyl peroxy)silane, respectively. The most highly preferred class is the acyl peroxides. The peroxides of this paragraph generally are used at a level between about 0.05% and 5% by weight of the urethane-acrylate monomer, preferably 0.01% to 3% by weight.

The peroxides of the preceding paragraph, and most particularly the acyl peroxides, are most commonly activated by the use of an organic amine, generally having a molecular weight less than about 800. While primary, secondary or tertiary alkyl, aryl or alkyl/aryl amines can be used, the preferred amines are amines of the formula:

$$ArNr^9R^{10}$$

where Ar is as defined above, preferably being $C_6H_5$ or a $C_1$—$C_4$ alkyl substituted $C_6H_5$; and each of $R^9$ and $R^{10}$ is hydrogen or a $C_1$ to $C_4$ alkyl group. Preferably each of $R^9$ and $R^{10}$ is methyl or ethyl.

The amines are used at the same level described in the preceding paragraph for the peroxides. In addition to the above ingredients, other ingredients known in the dental filling composition art may be added. The common additive, and one which is essential in most dental filling compositions, is an inorganic filler material, such as finely ground glass powder. The preferred filler is an aluminum borosilicate glass, most preferably having an average particle size which is less than about 40 microns. The inorganic filler frequently comprises a significant, and even a major, portion of dental filling composites. For example, they can comprise from about 40 to about 95 percent by weight of the total composition, preferably 70 to 90% by weight.

It is frequently desirable to add low levels, such as up to about 500 parts per million by weight, of a free-radical or uv stabilizer, many of which are shown in the art, to prevent spurious polymerization of the composition prior to the time of its intended use. Suitable free-radical stabilizers are hydroquinone, p-benzoquinone, butylate of hydroxy toluene and butylate of hydroxyanisole. It also may be desirable to modify the compositions by the addition of lower viscosity polymerizable ingredients, most commonly lower viscosity acrylate esters. Typical examples are hydroxyethyl methacrylate, hydroxypropyl methacrylate, trimethylolpropane trimethacrylate, butyleneglycol dimethacrylate and polyethyleneglycol dimethacrylate. Many other acrylate esters are known in the art, and essentially any of said esters can be used for purposes herein. An amount of lower viscosity acrylate ester is used which is necessary to produce the desired viscosity, but when the ester selected contains only one acrylic functional group, the amount used should not exceed the weight of the urethane-acrylate ester since the hardness or durability of the final product could be affected.

Other materials, such as adhesive agents, plasticizers, pigmenting agents, etc., can be used if desired.

In discussing the use ratios of the various components, the bulk of the composition should be composed of at least 5% by weight urethane acrylate monomer, plus initiator system and inorganic filler. All other ingredients preferably do not comprise more than about 30 percent by weight of the composition.

late monomer, to facilitate mixing at the time of use. The balance of weight of use between the two components is a matter of choice dependent upon the systems used, and determination thereof is well within the province of the reasonably skilled chemist.

The compositions of this invention have been found to be easily prepared and used. When placed and cured in a tooth cavity, the composition forms hard and durable adhesive bonds to normal tooth structure. The cured composition is abrasion resistant, and can easily be formulated to match the tooth color and texture.

EXAMPLES

The invention will now be illustrated by the following description of specific embodiments thereof, given by way of example only.

The monomers used in the Examples are monomers A and B, and have the formulae:

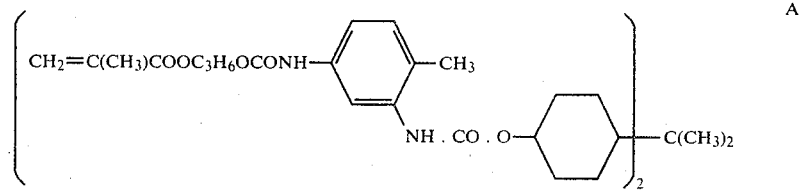

For a system which is to be initiated by a uv mechanism, it is generally preferable to add the uv activated free-radical initiator directly to the mixture of urethane acrylate monomer and other ingredients as described herein. This provides a one-component system which can be used directly to fill the apertures or cavities in the teeth and immediately activated with uv light. In those systems which are not to be uv activated, it is possible to prepare systems which can contain all necessary curing agents as a single component composition, such as one in which the cure is via a hydroperoxide/amine initiator system. Such one-component peroxy systems tend to the be excessively slow; a far more preferable approach is to separate either the peroxy compound or the activator therefor into a second component which is to be added immediately prior to use. In this fashion, compounds can be selected and used in such amount as to provide much more rapid cure. It is for this reason that a certain number of systems enumerated above have been specified as preferred compositions.

When the two-component system is to be utilized, it is preferable that the peroxy compound be used as an additive at the time of use since in this way the most highly stable compositions can be prepared. The dentist then can measure out the appropriate quantities of each of the two components and mix them, directly apply them to the aperture or cavity, and within a short time such as one to 30 minutes, a hard and durable filling composition will be formed in the tooth. When the two-component system is utilized, it is generally desirable to mix the peroxy ingredient with a plasticizer or a polymerizable acrylate ester, including a urethane acryand

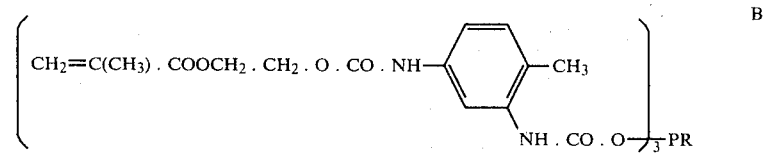

in which PR represents a propylene triol oligomer (average molecular weight 2500) residue, i.e., devoid of its three hydroxyl groups.

EXAMPLE I

A dental filling composition was prepared by blending the following ingredients, expressed on a parts by weight basis:

| 1  | Monomer A                          | 14    |
|----|------------------------------------|-------|
| 2  | Monomer B                          | 7     |
| 3  | Methacrylic Acid                   | 0.8   |
| 4  | Methacryloxy trimethoxysilane      | 0.66  |
| 5  | Naphthoquinone                     | 0.33  |
| 6  | Cucene hydroperoxide               | 0.166 |
| 7  | Benzophenone                       | 1.6   |
| 8  | Hydroxyethyl methacrylate          | 14    |
| 9  | Uniflex 330                        | 15    |
| 10 | Glass powder (dental quality) q.s.ad. | 100 |

Ingredients 3 and 4 are adhesion promoters, 5 is a stabilizer, 6 is a free-radical inhibitor, 7 is the photo-initiated carbonyl compound, 8 and 9 are viscosity regulators, 9 being a proprietary product of Union Camp Corporation, Wayne, New Jersey, U.S.A. which comprises poly(butylene sebacate), and 10 is a mechanical extender and toughener as used in conventional dental filling compositions.

The composition was applied to a prepared tooth cavity, molded into the required shape, and sprayed with a methyl 2-cyanoacrylate adhesive composition which immediately hardened to a transparent film. The covered composition was then iradiated for 60 seconds at 12 inches distance using a lighted Philips 125 watt HPK high pressure mercury vapor ultraviolet-emitting lamp. Under this treatment the composition rapidly cured, yielding a highly satisfactory dental filling.

EXAMPLE II

A two-part dental filling composition above-mentioned was prepared using the following ingredients, expressed as parts by weight:

| FIRST PART | | |
| --- | --- | --- |
| 1 Monomer A | 14 | |
| 2 Monomer B | 8 | |
| 3 Methacrylic acid | 1 | |
| 4 Methacryloxy trimethoxysilane | 0.66 | |
| 5 Naphthaquinone | 0.3 | |
| 6 N,N-dimethyl-p-toluidine | 0.5 | |
| 7 Hydroxypropyl methacrylate | 14 | |
| 8 Uniflex 330 | 10 | |
| 9 Glass Powder, q.s.ad | 100 | |
| SECOND PART | | |
| 10 Dibenzoyl peroxide | 5 | |
| 11 Uniflex 330 | 45 | |
| 12 Glass Powder | 50 | |

10 parts by weight of the First Part were mixed with one part by weight of the Second Part. The mixture was applied to a prepared tooth cavity, where it was molded into the desired shape. After 15 minutes the filling was sufficiently hard for normal use, and was a highly satisfactory dental filling by standard professional criteria.

The setting time of the composition of this Example can be varied by altering the proportions of the two parts. Thus, First and Second Parts in the above ratio of 10:1 give a setting time of 15 minutes; a 5:1 ratio gives 5 minutes and a 20:1 ratio gives about 30 minutes.

The Invention is not limited by or to the details of the specific embodiments described in the Examples, many of which can be substantially varied in detail without departing from the scope of the invention.

We claim:

1. A dental filling composition which comprises: a mixture of
   (1) polymerizable acrylate ester monomers, the structure of one of which conforms to (a) the formula

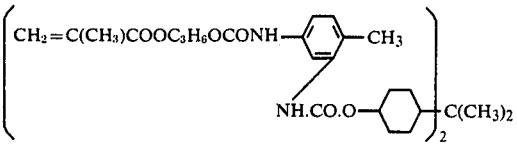

and the other structure which conforms to (b) the formula

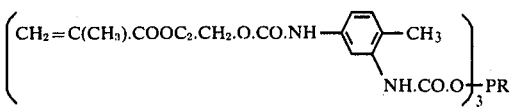

wherein PR represents a propylene triol oligomer residue;
   (2) about 0.1 to about 7 percent by weight of a free radical polymerization initiator, based upon the weight of the mixture of the two monomers; and
   (3) about 40 to 95 percent by weight glass powder filler, based upon the weight of the composition.

* * * * *